(12) United States Patent
Siggel et al.

(10) Patent No.: US 7,641,807 B2
(45) Date of Patent: Jan. 5, 2010

(54) DIRECT PROCESS FOR THE MANUFACTURE OF TETRAALKYLAMMONIUM TETRAFLUOROBORATE-CONTAINING ELECTROLYTE COMPOSITIONS

(75) Inventors: Alfred Siggel, Seelze (DE); Michael Fooken, Seelze (DE); Christian Liepelt, Lehrte (DE); Michael Theissen, Hannover (DE)

(73) Assignee: Honeywell International Inc, Morristown, NJ (US)

( * ) Notice: Subject to any disclaimer, the term of this patent is extended or adjusted under 35 U.S.C. 154(b) by 468 days.

(21) Appl. No.: 10/533,463

(22) PCT Filed: Oct. 31, 2003

(86) PCT No.: PCT/EP03/12184

§ 371 (c)(1), (2), (4) Date: Dec. 4, 2006

(87) PCT Pub. No.: WO2004/039761

PCT Pub. Date: May 13, 2004

(65) Prior Publication Data

US 2007/0097598 A1    May 3, 2007

(30) Foreign Application Priority Data

Oct. 31, 2002   (DE) .............................. 102 50 808

(51) Int. Cl.
C07C 209/00   (2006.01)
C07C 211/63   (2006.01)
H01G 9/02     (2006.01)

(52) U.S. Cl. .................. 252/62.2; 564/296; 564/291; 564/8; 429/188; 429/199; 429/201; 429/304; 429/307

(58) Field of Classification Search ............... 252/62.2; 564/296, 291, 8; 361/503–505, 523, 525–527; 429/188, 300, 304, 307, 201, 199
See application file for complete search history.

(56) References Cited

U.S. PATENT DOCUMENTS

| 4,877,695 A | 10/1989 | Cipriano et al. ............. 429/102 |
| 5,086,374 A | 2/1992 | MacFarlane et al. ........ 361/525 |
| 5,418,682 A * | 5/1995 | Warren et al. ............... 361/502 |
| 5,705,696 A | 1/1998 | King, Jr. ..................... 564/296 |
| 6,852,229 B2 * | 2/2005 | Mehnert et al. ............. 210/634 |
| 6,853,472 B2 * | 2/2005 | Warner et al. ............... 359/270 |

FOREIGN PATENT DOCUMENTS

| JP | 63 174954 | | 7/1988 |
| JP | 10 087574 | | 4/1998 |
| JP | 10-87574 | * | 4/1998 |
| JP | 2000-86671 | * | 3/2000 |
| JP | 2002-047255 | | 2/2002 |

OTHER PUBLICATIONS

Translation for JP 10-87574.*
Kobayashi et al., *Synthetic Metals*, 18 (1987) pp. 619-624.

* cited by examiner

*Primary Examiner*—C. Melissa Koslow
(74) *Attorney, Agent, or Firm*—Carrie Beatus

(57) ABSTRACT

Process for the manufacture of tetraalkylammonium tetrafluoroborate-containing electrolyte compositions characterized in that said process comprises step (i): (i) mixing of at least one tetraalkylammonium halide with at least one metal tetrafluoroborate in at least one organic solvent, which is partially or completely miscible with water.

7 Claims, No Drawings

DIRECT PROCESS FOR THE MANUFACTURE OF TETRAALKYLAMMONIUM TETRAFLUOROBORATE-CONTAINING ELECTROLYTE COMPOSITIONS

CROSS-REFERENCE TO RELATED APPLICATIONS

This application is the U.S. National Phase entry of PCT/EP2003/012184, filed Oct. 31, 2003, which claims priority to German Patent Application No. DE 10250808.9, filed Oct. 31, 2002, which is incorporated herein by reference.

The invention relates to a direct process for the manufacture of tetraalkylammonium tetrafluoroborate-containing electrolyte compositions by reacting tetraalkylammonium halides with metal tetrafluoroborates in an organic solvent, which is miscible with water. Furthermore, the invention relates to electrolyte compositions, which can be produced according to the new process as well as the use of said compositions in electrochemical cells and energy storage devices.

Non-aqueous electrolyte compositions are used in numerous applications as, for instance, electrochemical cells or capacitors with high capacity (ultra- or supercapacitor) which can be used as energy storage device. It is already known to apply for said application electrolyte compositions, which contain tetraalkylammonium tetrafluoroborates (U.S. Pat. No. 5,086,374; Kobayashi et al. in Synthetic Metals, 18, (1987) 619-624).

For the manufacture of said tetraalkylammonium tetrafluoroborate-containing electrolyte compositions said pure quaternary ammonium salts are dissolved in a solvent with high solvent power and high chemical and thermal stability, for instance 1,2-propylene carbonate (U.S. Pat. No. 5,705,696).

Said patent discloses two processes for the manufacture of tetraalkylammonium tetrafluoroborates. In one of said processes tetraalkylammonium halides are reacted with metal tetrafluoroborates in an aqueous medium, wherein in a second reaction step metal halide, which is formed as a by-product, is separated off by means of membrane dialysis. If necessary said reaction step has to be repeated several times to achieve the required purity. Subsequently said tetraalkylammonium tetrafluoroborate can be isolated from the aqueous solution by drying, for instance by freezing drying. However, it is possible to remove the water by azeotropic distillation with an organic solvent, wherein the product can be obtained as residue.

In the second process tetraalkylammonium tetrafluoroborate, which is formed in aqueous medium from tetraalkylammonium halide and alkali metal tetrafluoroborate is extracted with an organic solvent, which is immiscible with water. The alkali metal halide, which is formed as by-product, remains dissolved in the aqueous phase. By evaporating the organic phase said quaternary ammonium tetrafluoroborate can be obtained in pure form. Preferably chlorinated hydrocarbons are used for the extracting process, for instance methylene chloride.

However, for technical processes said two-step reactions for the manufacture of tetraalkylammonium tetrafluoroborate-containing electrolyte compositions are costly and therefore uneconomic, because in a first step starting with tetraalkyl ammonium halide the tetraalkyl ammonium tetrafluoroborate is produced in pure form and isolated. Afterwards in a second step it is used for the production of the electrolyte composition by dissolving it into a suitable solvent. It is known that the use of chlorinated hydrocarbons as solvents is not harmless for toxicological reasons.

It was the object of the present invention to provide a process for the manufacture of tetraalkylammonium tetrafluoroborate-containing electrolyte compositions, which can be carried out easier and therefore more economic than said processes which are described as prior art.

This object could be achieved by reacting tetraalkylammonium halides with metal tetrafluoroborates in organic solvents, which are miscible with water, wherein the tetraalkylammonium tetrafluoroborate-containing electrolyte compositions are obtained.

Therefore, the subject-matter of the invention is a process for the manufacture of tetraalkylammonium tetrafluoroborate-containing electrolyte compositions, characterized in that said process comprises step (i):

(i) mixing at least one tetraalkylammonium halide with at least one metal tetrafluoroborate in at least one organic solvent which is partially or completely miscible with water.

In contrast to the two-step processes of the prior art the new process provides said tetraalkylammonium tetrafluoroborate-containing electrolyte composition in one step from tetraalkylammonium halide as the starting material. Therefore, said process can be described as a direct process. It can be carried out in a simple manner what is extraordinary advantageous for the technical application.

The quaternary ammonium halides which are used as educts for the new process are known or can be manufactured according to known processes. For instance, said ammonium halides can be produced by reacting trialkylamines with alkyl halides. It is possible to use the fluorides, chlorides, bromides as well as iodides. It is preferred to use the chlorides or bromides.

Further, it is preferred that in said tetraalkylammonium halides the alkyl radicals contain independently from each other of from one to ten carbon atoms.

Examples for preferred tetraalkylammonium halides are tetraethylammonium chloride or -bromide, methyltriethylammonium chloride or bromide, methyltrioctylammonium chloride or -bromide.

It is preferred to use as solvents which are partially or completely miscible with water those ones which can pick up at least 5% by weight of water without separation of the phases, wherein the total amount of organic solvent and water is 100% by weight. Further, the solvents which are used for the tetraalkylammonium tetrafluoroborate of the invention should have a high solvent power as well as a high chemical and thermal stability.

Suitable solvents are preferably selected from the group comprising nitrites, for example acetonitrile, dinitriles, for example malonic dinitrile, alkylcarbonates, for example diethyl carbonate, alkylene carbonate, for example ethylene carbonate or 1,2-propylene carbonate, as well as lactones, for example γ-butyrolactone.

Particularly preferred solvents are acetonitrile, 1,2-propylene carbonate as well as γ-butyrolactone.

Furthermore, it is possible to use derivatives of alkylene glycols, dialkylene glycols, trialkylene glycols, polyalkylene glycols, sulfoxides, substituted amides, substituted amines, cyclic ethers, lactames, anhydrides, esters, urethanes, ureas, lactate esters, esters, wherein the alcoholic component contains one or more nitrile groups, diketones, as well as siloxanes, provided said derivatives are partially or completely miscible with water.

It is preferred to use as metal tetrafluoroborates the tetrafluoroborates of the alkali metals, for instance sodium or potassium tetrafluoroborate, as well as the tetrafluoroborates of the earth alkali metals, for instance calcium or magnesium tetrafluoroborate.

In particular it is preferred to use sodium and potassium tetrafluoroborate.

The new process can be carried out in an extraordinary simple manner. Typically, at least one tetraalkylammonium halide and at least one metal tetrafluoroborate are introduced as solids into said at least one organic solvent. However, it is also possible to mix the educts in suspended form, wherein small amounts can already exist in dissolved form. It is possible to stir the mixture in order to achieve a thorough mixing.

It is preferred to mix the at least one tetraalkylammonium halide and the at least one metal tetrafluoroborate in a molar ratio of from 2:1 to 1:5.

During the mixing process an ion exchange reaction takes place, wherein the tetraalkylammonium tetrafluoroborate as well as the metal halide are formed. If different tetraalkylammonium halides and/or different metal tetrafluoroborates are used at the same time, different tetraalkylammonium tetrafluoroborates and/or metal halides are formed. Said tetraalkylammonium tetrafluoroborate is dissolving into said organic solvent, wherein the metal halide precipitates. The reaction is already starting at relatively low temperatures. It is possible to work at higher temperatures in order to enhance the reaction, for instance at the boiling point of said organic solvent.

It is preferred to use a reaction temperature of from −50° C. to +240° C.

During the ion exchange reaction the electric conductivity is increased due to the good solubility of said tetraalkylammonium tetrafluoroborate in said organic solvent, wherein the formation of said salts can be proved.

The concentration of the produced tetraalkylammonium tetrafluoroborate in the solvent can be adjusted to the respective requirements. In general, the concentration is selected in a way not to cross the limit of saturation. Then said tetrafluoroborate remains completely dissolved.

It is preferred to select such concentrations of the educts that the at least one tetraalkylammonium tetrafluoroborate which is formed after the mixing process is existing in the solvent in a concentration of preferably from 0.1 to 5.0 moles/l. In particular a concentration of from 0.5 to 2.0 moles/l is preferred.

It is preferred to separate off parts of the formed metal halide or the formed metal halides which are insoluble in said solvent. Said separation can be achieved by the known methods, for instance filtration or centrifugation.

If necessary, the formed mixture can be dried according to the known methods. For instance, it is possible to use for the drying process freezing drying, azeotropic distillation, molecular sieves, sodium sulfate, magnesium sulfate, alkali metals and earth alkali metals as well as the hydrides thereof or organic acrylates. The drying process can be carried out before or after the separation or before and after the separation of the insoluble parts of the metal halide.

Therefore, certain embodiments of the invention are characterized in that said process comprises at least one of the steps (ii) and (iii):
 (ii) separation of metal halide,
 (iii) drying.

Due to the high solvent power of the used organic solvent as well as the mediating properties concerning the solubility of the tetraalkylammonium salts the at least one tetraalkylammonium tetrafluoroborate-containing electrolyte composition, however, contains always parts of dissolved metal halide respectively metal halides. It is preferred that said parts are present in a concentration of from 10 ppm to 2.0% by weight, in particular of from 15 ppm to 1.0% by weight, wherein said concentration range refers to an electrolyte residue being free from solvent.

It was not predictable and is therefore extraordinarily surprising that said parts do not impair the application of the electrolyte composition. Therefore, it is an extraordinary advantage of the new process of the invention that said parts of the mixture need not to be removed by further purification steps, but can remain dissolved in the mixture.

Therefore, the electrolyte compositions which are produced according to the new direct process are delimited from those ones, which are described as prior art by dissolving the pure tetraalkylammonium tetrafluoroborate into solvents. Said tetraalkylammonium tetrafluoroborates have to be essentially free from halides. Typically, the amount of halide of said produced electrolyte compositions must be below 10 ppm related to the dry residue, because otherwise one has to take into account corrosion of the electrochemical cells or energy storage devices.

Therefore, another object of the invention are tetraalkylammonium tetrafluoroborate-containing electrolyte compositions characterized in that they are obtainable by a process comprising the step (i):
 (i) mixing of at least one tetraalkylammonium halide, preferably characterized in that the alkyl groups contain independently from each other from 1 to 10 carbon atoms, with at least one metal tetrafluoroborate, preferably an alkali metal tetrafluoroborate, and preferably in a tetraalkylammonium halide:metal tetrafluoroborate molar ratio of from 2:1 to 1:5, in at least one organic solvent, preferably at least one or organic solvent is selected from the group consisting of nitrites, dinitriles, alkyl carbonates, alkylene carbonates, and lactones which is partially or completely miscible with water, wherein said mixing is preferably carried out at a temperature of from −50° C. to +240° C.

In certain preferred embodiments, the organic solvent is acetonitrile, 1,2-propylene carbonate or γ-butyrolactone and that 1 to 4 of the alkyl groups of the at least one tetraalkylammonium tetrafluoroborate are ethyl groups. In certain preferred embodiments, the method further comprises at least one of the following reaction steps: (ii) separation of metal halide; and (ii) drying. In certain preferred embodiments, the electrolytes produced by this method are characterized in that said compositions are noncorrosive in electrochemical cells or capacitors.

Another subject-matter of the invention is also the use of the tetraalkylammonium tetrafluoroborate-containing electrolyte compositions per se or the tetraalkylammonium tetrafluoroborate-containing electrolyte compositions produced according to the process of the invention in electrochemical cells or capacitors. It is preferred to use said compositions in capacitors with high capacity (ultra- or supercapacitors) which are used as energy storage devices. In a typical construction of such a capacitor two metallic energy collectors are separated by porous electrodes, typically of carbon, which in turn are separated by a porous, non-conducting separator layer. The pores in the electrodes and separator are filled with an electrolyte. Then a current is applied to the electrodes at a voltage below that at which an electrolytic reaction will take place. As a result, charged ions, typically from dissociation of salts in the electrolyte, accumulate on the surfaces of the electrodes, creating a voltage difference. Said voltage difference can produce a current when desired (U.S. Pat. No. 5,705,696).

In particular electrolyte compositions of tetraethylammonium tetrafluoroborate in acetonitrile, methyltriethylammonium tetrafluoroborate in acetonitrile, methyltriethylammonium tetrafluoroborate in 1,2-propylene carbonate, tetraethylammonium tetrafluoroborate in 1,2-propylene carbonate as well as tetraethylammonium tetrafluoroborate in γ-butyrolactone which are produced according to the new process are suitable for said application. The concentration of said quaternary ammonium tetrafluoroborate is preferably of from 0.5 to 2.0 mol/l. In particular, the concentration is of from 0.75 to 1.5 mol/l.

The following electrolyte compositions are also producible according to the new process starting with following educt compositions (tetraalkylammonium halide/metal tetrafluoroborate/solvent/reaction temperature/concentration of the tetraalkylammonium tetrafluoroborate in the solvent [mol/l]):

tetraethylammonium bromide/potassium tetrafluoroborate/acetonitrile/20° C./1;
methyltriethylammonium chloride/potassium tetrafluoroborate/acetonitrile/20° C./1;
methyltriethylammonium bromide/potassium tetrafluoroborate/1,2-propylene carbonate/20° C./1;
tetraethylammonium bromide/potassium tetrafluoroborate/1,2-propylene carbonate/20° C./1;
tetraethylammonium chloride/potassium tetrafluoroborate/1,2-propylene carbonate/20° C./1;
methyltriethylammonium chloride/potassium tetrafluoroborate/1,2-propylene carbonate/20° C./1;
methyltriethylammonium bromide/potassium tetrafluoroborate/1,2-propylene carbonate/20° C./1;
tetraethylammonium chloride/potassium tetrafluoroborate/γ-butyrolactone/20° C./1;
tetraethylammonium bromide/potassium tetrafluoroborate/γ-butyrolactone/20° C./1;
methyltriethylammonium chloride/potassium tetrafluoroborate/γ-butyrolactone/20° C./1;
methyltriethylammonium bromide/potassium tetrafluoroborate/γ-butyrolactone/20° C./1;
tetraethylammonium chloride/sodium tetrafluoroborate/acetonitrile/20° C./1;
tetraethylammonium chloride/lithium tetrafluoroborate/acetonitrile/20° C./1;
tetraethylammonium chloride/calcium tetrafluoroborate/acetonitrile/20° C./1;
tetraethylammonium chloride/magnesium tetrafluoroborate/acetonitrile/20° C./1;
tetraethylammonium chloride/potassium tetrafluoroborate/acetonitrile/82° C./1;
methyltriethylammonium chloride/potassium tetrafluoroborate/1,2-propylene carbonate/240° C./1;
tetraethylammonium chloride/potassium tetrafluoroborate/γ-butyrolactone/204° C./1;
tetraethylammonium chloride/potassium tetrafluoroborate/acetonitrile/20° C./0, 1;
tetraethylammonium chloride/potassium tetrafluoroborate/acetonitrile/20° C./2;
tetraethylammonium bromide/potassium tetrafluoroborate/1,2-propylene carbonate/20° C./2;
tetraethylammonium bromide/potassium tetrafluoroborate/γ-butyrolactone/20° C./2,
tetraethylammonium bromide/potassium tetrafluoroborate/acetonitrile/20° C./0.9;
tetraethylammonium bromide/potassium tetrafluoroborate/acetonitrile/20° C./1.4;

The invention is now explained by an example.

EXAMPLE

Production of a 1-Molar Tetraethylammonium Tetrafluoroborate-Containing Electrolyte Composition in Acetonitrile 17.26 g tetraethylammonium chloride (96%) and 12.98 g potassium tetrafluoroborate (97%) were weighed out in a 200 ml flask and filled up with 100 ml acetonitrile. After stirring for 15 minutes at 20° C. the solution was filtered and the conductivity was estimated with a commercially available apparatus of the company Siemens. Said conductivity was measured to give 54.7 mS/cm.

A sample of said electrolyte composition was evaporated and the chloride concentration of the residue was estimated. Said chloride concentration was 0.71% by weight.

The invention claimed is:

1. A process for the manufacture of tetraalkylammonium tetrafluoroborate-containing electrolyte compositions, characterized in that said process comprises step (i):
    (i) mixing of at least one tetraalkylammonium halide with at least one metal tetrafluoroborate in at least one organic solvent selected from the group consisting of nitrites, dinitriles, alkyl carbonates, alkylene carbonates, and lactones, which is partially or completely miscible with water.

2. The process as claimed in claim 1, characterized in that the alkyl groups of the at least one tetraalkylammonium halide contain independently from each other from 1 to 10 carbon atoms.

3. The process as claimed in claim 1, characterized in that the at least one metal tetrafluoroborate is an alkali metal tetrafluoroborate.

4. The process as claimed in claim 1, characterized in that the at least one tetraalkylammonium halide and the at least one metal tetrafluoroborate are mixed in a molar ratio of from 2:1 to 1:5.

5. The process as claimed in claim 4, characterized in that the mixing process is carried out at a temperature of from −50° C. to +240° C.

6. The process as claimed in claim 1, characterized in that the at least one organic solvent is acetonitrile, 1,2-propylene carbonate or γ-butyrolactone and that 1 to 4 of the alkyl groups of the at least one tetraalkylammonium tetrafluoroborate are ethyl groups.

7. The process as claimed in claim 1, characterized in that said process further comprises at least one of the reaction steps (ii) and (iii):
    (ii) separation of metal halide,
    (iii) drying.

* * * * *

UNITED STATES PATENT AND TRADEMARK OFFICE
CERTIFICATE OF CORRECTION

PATENT NO. : 7,641,807 B2  Page 1 of 1
APPLICATION NO. : 10/533463
DATED : January 5, 2010
INVENTOR(S) : Siggel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 555 days.

Signed and Sealed this

Sixteenth Day of November, 2010

David J. Kappos
*Director of the United States Patent and Trademark Office*